(12) United States Patent
Suh

(10) Patent No.: US 10,034,698 B2
(45) Date of Patent: *Jul. 31, 2018

(54) ORTHOPEDIC PLATE BLOCKING ASSEMBLY

(71) Applicant: GLOBUS MEDICAL, INC., Audubon, PA (US)

(72) Inventor: Sean Suh, Morganville, NJ (US)

(73) Assignee: Globus Medical, Inc., Audubon, PA (US)

( * ) Notice: Subject to any disclaimer, the term of this patent is extended or adjusted under 35 U.S.C. 154(b) by 62 days.

This patent is subject to a terminal disclaimer.

(21) Appl. No.: 15/214,806

(22) Filed: Jul. 20, 2016

(65) Prior Publication Data

US 2016/0324554 A1  Nov. 10, 2016

Related U.S. Application Data

(63) Continuation of application No. 14/876,997, filed on Oct. 7, 2015, now Pat. No. 9,421,055, which is a continuation of application No. 13/715,497, filed on Dec. 14, 2012, now Pat. No. 9,179,951, which is a continuation of application No. 13/275,979, filed on Oct. 18, 2011, now Pat. No. 8,357,185, which is a
(Continued)

(51) Int. Cl.
| | |
|---|---|
| *A61B 17/80* | (2006.01) |
| *A61B 17/58* | (2006.01) |
| *A61B 17/68* | (2006.01) |
| *A61B 17/70* | (2006.01) |
| *A61B 17/56* | (2006.01) |
| *A61B 17/88* | (2006.01) |

(52) U.S. Cl.
CPC .......... *A61B 17/8042* (2013.01); *A61B 17/56* (2013.01); *A61B 17/58* (2013.01); *A61B 17/68* (2013.01); *A61B 17/7059* (2013.01); *A61B 17/80* (2013.01); *A61B 17/8033* (2013.01); *A61B 17/8047* (2013.01); *A61B 17/88* (2013.01); *A61B 2017/564* (2013.01)

(58) Field of Classification Search
CPC ... A61B 17/56; A61B 2017/564; A61B 17/58; A61B 17/68; A61B 17/7059; A61B 17/80; A61B 17/8033; A61B 17/8038; A61B 17/8042; A61B 17/8047; A61B 17/8052; A61B 17/8057; A61B 17/88
See application file for complete search history.

(56) References Cited

U.S. PATENT DOCUMENTS

| | | | | |
|---|---|---|---|---|
| 7,875,062 | B2 * | 1/2011 | Lindemann | ........ A61B 17/8042 606/280 |
| 8,062,342 | B2 | 11/2011 | Suh | |

(Continued)

*Primary Examiner* — Larry E Waggle, Jr.

(57) ABSTRACT

In an exemplary embodiment, the present invention provides an orthopedic plate blocking assembly that can be used for the fixation or fastening of an orthopedic plate to bone tissue. In particular, the present invention, in one embodiment, provides an orthopedic plate having a plurality of cavities where each cavity is configured and dimensioned to receive a bone anchoring member. The orthopedic plate further provides a blocking mechanism having a plurality of blocking members that block the bone anchoring members to prevent the bone anchoring members from "backing out" of cavities once the bone anchoring members are finally seated in the cavities.

20 Claims, 2 Drawing Sheets

Related U.S. Application Data continuation of application No. 12/466,721, filed on May 15, 2009, now Pat. No. 8,062,342.

(56) References Cited

U.S. PATENT DOCUMENTS

| | | |
|---|---|---|
| 8,702,766 B2 | 4/2014 | Mueller |
| 2006/0200146 A1 | 9/2006 | Doubler et al. |
| 2011/0190770 A1 | 8/2011 | Suh |
| 2012/0035665 A1 | 2/2012 | Suh |
| 2013/0060291 A1 | 3/2013 | Petersheim |

* cited by examiner

ORTHOPEDIC PLATE BLOCKING ASSEMBLY

CROSS-REFERENCE TO RELATED APPLICATIONS

This patent application is a continuation of U.S. patent application Ser. No. 14/876,997, filed Oct. 7, 2015, which is a continuation of U.S. patent application Ser. No. 13/715,497, filed Dec. 14, 2012, now U.S. Pat. No. 9,179,951, which is a continuation application of U.S. patent application Ser. No. 13/275,979, filed Oct. 18, 2011, now U.S. Pat. No. 8,357,185, which is a continuation application of U.S. patent application Ser. No. 12/466,721, filed May 15, 2009, now U.S. Pat. No. 8,062,342, all of which are incorporated by reference herein in their entireties for all purposes.

FIELD OF THE INVENTION

The present invention is directed to orthopedic plates and, in particular, to a blocking assembly for securing an orthopedic plate to bone tissue.

BACKGROUND OF THE INVENTION

The use of orthopedic plates for correction of spinal deformities and for fusion of vertebrae is well known. Typically, a rigid plate is positioned to span bones or bone segments that need to be supported or immobilized with respect to one another. The orthopedic plate is fastened to the bone tissue with bone anchors or screws so that the plate remains in contact with and supports the bone or bone segments.

However, the structure of spinal elements presents unique challenges to the use of orthopedic plates for supporting or immobilizing vertebral bodies. Among the challenges involved in supporting or fusing vertebral bodies is the effective installation of an orthopedic plate that will resist migration despite the rotational and translational forces placed upon the plate resulting from spinal loading and movement. For a plate to work effectively in such an environment the bone anchors or screws must be properly positioned and anchored within the bone.

Furthermore, over time, it has been found that as a result of the forces placed upon the orthopedic plate and anchors resulting from the movement of the spine and/or bone deterioration, the orthopedic anchors can begin to "back out" from their installed position eventually resulting in the fasteners disconnecting from the plate.

As such, there exists a need for an orthopedic plate that provides for the proper placement of the bone anchor or screws and provides a mechanism where the bone anchors are blocked to prevent the anchors from "backing out" of their installed position

SUMMARY OF THE INVENTION

In an exemplary embodiment, the present invention provides an orthopedic plate blocking assembly that can be used for the fixation or fastening of an orthopedic plate to bone tissue. In particular, the present invention, in one embodiment, provides an orthopedic plate having a plurality of cavities where each cavity is configured and dimensioned to receive a bone anchoring member. The orthopedic plate also provides a blocking mechanism having a plurality of engaged blocking members that block the bone anchoring members to prevent the bone anchoring members from "backing out" of cavities once the bone anchoring members are finally seated in the cavities.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figures 1, 1A:
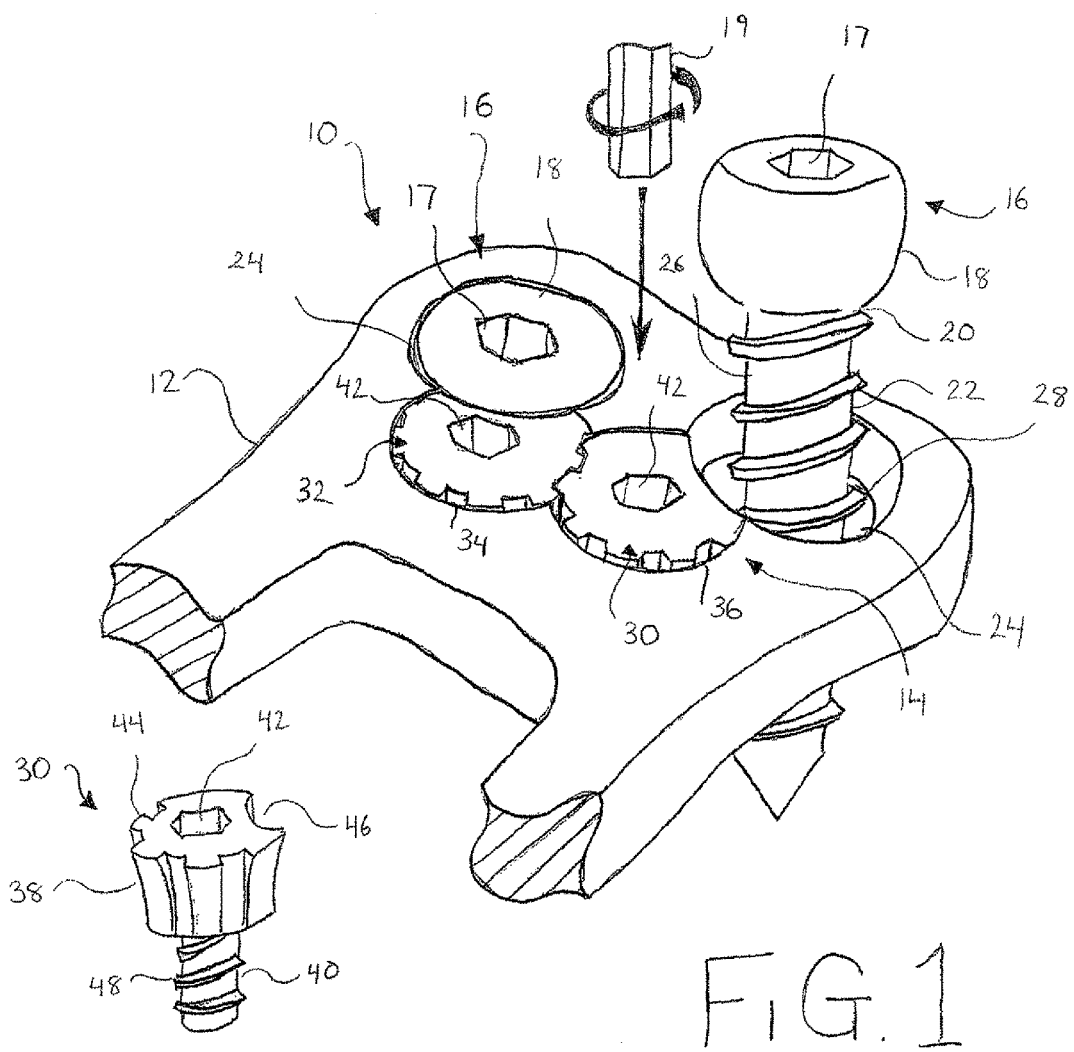
FIG. 1 is an exploded partial perspective view of one embodiment of an orthopedic plate blocking assembly.
FIG. 1A is a perspective view of a blocking gear included in the blocking assembly shown in FIG. 1.

With reference to FIG. 1, an embodiment of an orthopedic plate blocking assembly 10 is illustrated. Although not shown in the environment of use, the orthopedic plate blocking assembly 10 is adapted to be used for supporting and/or immobilizing adjacent bones or bone segments, such as vertebrae, in the spine. The blocking assembly 10 preferably includes an orthopedic plate 12, a blocking mechanism 14, and at least one bone screw 16. Even though only the bone screw 16 is identified as the fastening or anchoring element, it is contemplated that the fastening or anchoring element can be any of the following, including, but not limited to, a hook, a pin, or a nail. Further, although only two bone screws 16 are shown in FIG. 1, it is contemplated that the number of screws 16 will correlate to the size of the plate 12. For example, a smaller plate can include two to four screws whereas a larger plate can include six or more screws. The blocking assembly 10 is preferably constructed from any biocompatible material including, but not limited to, stainless steel, stainless tell alloys, titanium, titanium based alloys, or polymeric materials.

Looking at FIG. 1, in one embodiment, the screw 16 includes, concentric to a longitudinal axis, a head portion 18, a neck portion 20 and a shank portion 22. The head portion 18 connects to the shank portion 22 through the neck portion 20. Preferably, the head portion 18 of the screw 16 has a cavity 17 for receiving a driving instrument 19. The head portion 18 also has a generally spherical shape that is configured and dimensioned to be received within a correspondingly shaped cavity 24 in the orthopedic plate 12. The shape of the head portion 18 and the correspondingly shaped cavity 24 allow the screw 16 to pivot, rotate and/or move with respect to the orthopedic plate 12. In another embodiment, instead of allowing the screw 16 to pivot, rotate and/or move with respect to the orthopedic plate 12, the head portion 18 and the correspondingly shaped cavity 24 may be configured and dimensioned to keep the screw 16 in a fixed position with respect to the plate 12.

In an exemplary use, after the head portion 18 of the screw 16 is received in the cavity 24 of the orthopedic plate 12, the screw 16 can be pivoted, rotated or moved until the desired orientation with respect to the orthopedic plate 12 is met. This functionality allows the screw 16 to be anchored into the bone tissue at the desired orientation and placement with respect to the orthopedic plate 12 maximizing the ability of the plate 12 to resist migration in spite of the rotational and translational forces placed upon the plate from spinal loading and movement. One of ordinary skill in the art would recognize that the screw 16 is anchored into the bone tissue by driving the screw 16 into the bone tissue via driving instrument 19 interfacing with the cavity 17. The screw 16 is then blocked in place, which is discussed in detail below, in the cavity 24 of the orthopedic plate 12.

With continued reference to FIG. 1, in one embodiment, the neck portion 20 of the screw 16 integrally connects the head portion 18 with the shank portion 22. The shank portion 22 of the screw 16 includes a shaft 26 surrounded at least in part by a thread portion 28. In one embodiment, the diameter of the shaft 26 remains generally constant from a proximal end of the shaft 26 toward a distal end of the shaft 26. The constant diameter of a majority portion of the shaft 26 allows for optimal screw positioning when the screw 16 is inserted into a predetermined area in the bone tissue. The constant diameter also allows for varying the depth positioning of the screw 16 in the bone. For example, if a surgeon places the screw 16 into bone tissue at a first depth and decides the placement is more optimal at a second, shallower depth, the screw 16 can be backed out to the second depth and still remain fixed in the bone. In another embodiment, the diameter of the shaft 26 may vary along its length, including increasing in diameter from the proximal end to the distal end or decreasing in diameter from the proximal end to the distal end.

The thread portion 28 surrounding the shaft 26 extends, in a preferred embodiment, from the distal end of the shaft 26 to the neck portion 20. In another preferred embodiment, the thread portion 28 may extend along only a portion of shaft 26. The thread portion 28 is preferably a Modified Buttress thread but the thread can be any other type of threading that is anatomically conforming, including, but not limited to Buttress, Acme, Unified, Whitworth and B&S Worm threads.

In a preferred embodiment, the diameter of the thread portion 28 decreases towards the distal end of the screw 16. By having a decreased diameter thread portion 28 near the distal end of the screw 16, the screw 16 can be self-starting. In another preferred embodiment, screw 16 may also include at least one flute to clear any chips, dust, or debris generated when the screw 10 is implanted into bone tissue.

Figure 2:
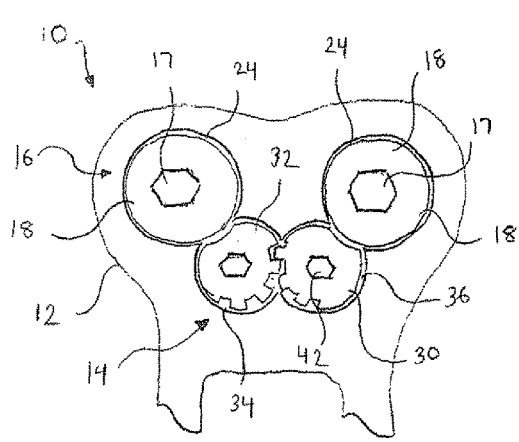
FIG. 2 is top view of the blocking assembly shown in FIG. 1 in an unblocked position.
Figure 3:
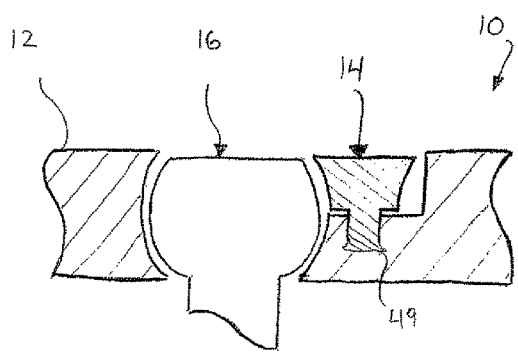
FIG. 3 is a schematic cross-sectional view of the blocking assembly shown in FIG. 1.

Turning to FIGS. 1-3, the blocking assembly 10 includes the blocking mechanism 14. The blocking mechanism 14 will block the screws 16 with respect to the orthopedic plate 12 thereby preventing the screws 16 from disengaging or "backing out" from the orthopedic plate 12. In one embodiment, the blocking mechanism 14 includes at least a leader blocking gear 30 and a follower blocking gear 32, each of which are configured and dimensioned to be received in openings 34, 36 in the orthopedic plate 12. Although only one leader blocking gear 30 and one follower blocking gear 32 are shown in FIG. 1, it is contemplated that for at least every two screws 16, there is at least one leader blocking gear 30 and at least one follower blocking gear 32. Alternatively, for multiple screws, there can be one leader blocking gear and a plurality of follower blocking gears. For example, there can be one leader blocking gear and plurality of follower blocking gears, where the leader blocking gear is positioned adjacent one screw, some of the plurality of follower blocking gears are positioned adjacent to the other screws, and some of the plurality of follower blocking gears serve to bridge the leader blocking gear and the follower blocking gears that are positioned adjacent the screws.

Focusing now on FIG. 1A, even though the following discussion is limited to the leader blocking gear 30, it is important to note that the following discussion is equally applicable to the follower blocking gear 32 as the structure of the follower blocking gear 32 is substantially identical to the leader blocking gear 30. In one embodiment, the leader blocking gear 30 has, concentric to a longitudinal axis, a head member 38 and a shaft member 40. The head member 38 preferably includes an opening 42 for receiving a driving instrument 19 and a variable diameter where the diameter of the head member 38 preferably increases in a non-linear fashion from the bottom end of the head member 38 to the top end of head member 38. The variable diameter of the head member 38 defines the shape of the head member 38 such that it can accommodate the spherically shaped head portion 18 of the screw 16 allowing the screw 16 to move with respect to the plate 12 but still block the screw 16 from disengaging or "backing out" from the plate 12. In one embodiment, the head member 38 also includes a plurality of gear teeth 44 extending along at least a portion of the circumference of the head member 38 and a cutout or access cut portion 46 extending along a portion of the circumference of the head member 38. In one embodiment, the shaft member 40 can include threading 48 extending along at least a portion of its length for engaging the orthopedic plate 12. Alternatively, as best seen in FIG. 3, the shaft member 40 may not have any threading, but can have a swaged tip 49 for engaging the orthopedic plate 12. The leader blocking gear 30 and the follower blocking gear 32 are positioned on the orthopedic plate 12 so that the gear teeth 44 on the blocking gears 30, 32 interdigitate allowing the leader blocking gear 30, when rotated, to rotate the follower blocking gear 32.

In an exemplary use of the orthopedic plate blocking assembly 10, the orthopedic plate 12 is oriented and placed in the area of treatment. The orthopedic plate 12 is then fastened to the bone tissue via at least one screw 16 which is received in at least one cavity 24 of the orthopedic plate 12. The screw 16 passes through the cavity 24 until the head portion 18 of the screw 16 is seated in the cavity 24. In an exemplary use, a plurality of screws 16 are received through the cavities 24 and are fastened to the bone tissue to fasten the plate 12 to the bone tissue.

As best seen in FIGS. 2-3, once the screws 16 are seated in the cavities 24, the screws 16 can be blocked to prevent the screws 16 from disengaging or "backing out" from the cavities 24 by actuating the blocking mechanism 14. Focusing on FIGS. 1 and 2, in one embodiment, a user actuates blocking mechanism 14 by engaging the opening 42 with the driving instrument 19 and using the driving instrument 19 to rotate the leader blocking gear 30 in a first direction from an unblocking position to a blocking position.

Figure 2A:
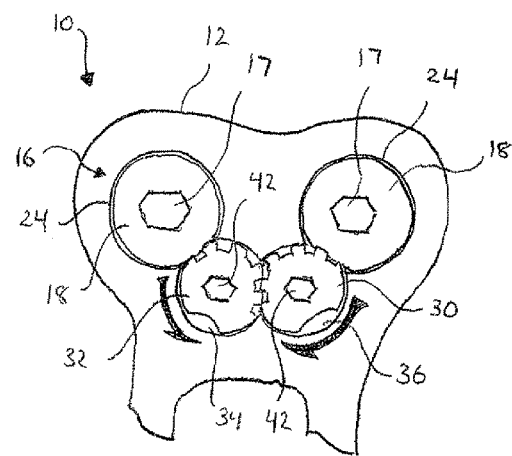
FIG. 2A is a top view of the blocking assembly of FIG. 1 in a blocking position.

In the unblocking position, shown in FIG. 2, the leader blocking gear 30 and the follower blocking gear 32 are positioned such that the access cut portions 46 of the blocking gears 30, 32 are aligned with the cavities 24 allowing the screws 16 to enter and exit from cavities 24. As the leader blocking gear 30 is rotated from an unblocking position to a blocking position, the follower blocking gear 32 also rotates from an unlocked or unblocking position to a blocking position since the gear teeth 44 on the blocking gear 30 are engaged with the gear teeth 44 on the follower blocking gear 32. The leader blocking gear 32 and the follower blocking gear 34 are rotated until the access cut portions 46 of the blocking gears 30, 32 are no longer aligned with the cavities 24. This is the blocking position of the blocking gears 30, 32 and can best be seen in FIGS. 2A and 3, where a portion of the head members 38 of the blocking gears 30, 32 are blocking the screws 16 from disengaging or "backing out" from cavities 24.

In order to set the blocking gears 30, 32 back into the unblocking position, the blocking gears 30, 32 can be rotated in a second direction, which is opposite to the first direction, until the access cut portions 46 of the blocking gears 30, 32 are again aligned with the cavities 24 allowing the screws 16 to be removed from the plate 12. Alternatively, the blocking gears 30, 32 can be further rotated in the first direction until the access cut portions 46 of the blocking gears 30, 32 are again aligned with the cavities 24 allowing the screws 16 to be removed from the plate 12.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An orthopedic system comprising:
an orthopedic plate;
a bone screw received in the orthopedic plate;
a leader blocking gear in contact with a follower blocking gear, wherein at least one of the leader blocking gear and the follower blocking gear is configured to prevent backout of the bone screw, wherein the leader blocking gear comprises a head member and a shaft member, wherein the head member has a variable diameter such that its upper surface is larger in diameter than its lower surface.

2. The orthopedic system of claim 1, wherein the leader blocking gear further comprises gear teeth extending along at least a portion of the head member.

3. The orthopedic system of claim 2, wherein the follower blocking gear also comprises gear teeth, wherein the gear teeth of the leader blocking gear and the gear teeth of the follower blocking gear are configured to interdigitate upon rotation of the leader blocking gear.

4. The orthopedic system of claim 1, wherein the head member of the leader blocking gear comprises a circumference and a cutout portion extending therein.

5. The orthopedic system of claim 4, wherein the head member of the leader blocking gear comprises gear teeth.

6. The orthopedic system of claim 1, wherein the follower blocking gear also comprises a head member.

7. The orthopedic system of claim 6, wherein the head member of the leading blocking gear and the head member of the following blocking gear comprise cutout portions.

8. The orthopedic system of claim 1, further comprising a second bone screw, wherein the follower blocking gear is configured to prevent backout of the second bone screw.

9. The orthopedic system of claim 8, wherein the leader blocking gear and the follower blocking gear each include threading and gear teeth.

10. The orthopedic system of claim 9, wherein the leader blocking gear and the follower blocking gear each include a cutout portion.

11. An orthopedic system comprising:
an orthopedic plate;
a bone screw received in the orthopedic plate;
a leader blocking gear in contact with a follower blocking gear, wherein the leader blocking gear is configured to prevent backout of the bone screw, wherein the leader blocking gear comprises a head member and a shaft member, wherein the leader blocking gear comprises threading and gear teeth.

12. The orthopedic system of claim 11, wherein the head member of the leader blocking gear further comprises a variable diameter.

13. The orthopedic system of claim 12, wherein the follower blocking gear also comprises gear teeth, wherein the gear teeth of the leader blocking gear and the gear teeth of the follower blocking gear are configured to interdigitate upon rotation of the leader blocking gear.

14. The orthopedic system of claim 11, wherein the head member of the leader blocking gear comprises a circumference and a cutout portion extending therein.

15. The orthopedic system of claim 14, wherein the head member of the leader blocking gear has an upper surface having a larger diameter than a lower surface.

16. The orthopedic system of claim 11, wherein the follower blocking gear also comprises a head member.

17. The orthopedic system of claim 16, wherein the head member of the leading blocking gear and the head member of the following blocking gear comprise cutout portions.

18. The orthopedic system of claim 11, further comprising a second bone screw, wherein the follower blocking gear is configured to prevent backout of the second bone screw.

19. The orthopedic system of claim 18, wherein the follower blocking gear includes threading and gear teeth.

20. The orthopedic system of claim 19, wherein the leader blocking gear and the follower blocking gear each include a cutout portion.

* * * * *